(12) United States Patent
Wang et al.

(10) Patent No.: US 9,505,677 B2
(45) Date of Patent: Nov. 29, 2016

(54) STEAM CRACKING PROCESSES

(71) Applicants: CHINA PETROLEUM & CHEMICAL CORPORATION, Beijing (CN); BEIJING RESEARCH INSTITUTE OF CHEMICAL INDUSTRY, CHINA PETROLEUM & CHEMICAL CORP, Beijing (CN)

(72) Inventors: Guoqing Wang, Beijing (CN); Lijun Zhang, Beijing (CN); Yonggang Zhang, Beijing (CN); Junjie Liu, Beijing (CN); Zhiguo Du, Beijing (CN); Xianfeng Zhou, Beijing (CN); Wei Li, Beijing (CN); Cong Zhou, Beijing (CN)

(73) Assignees: China Petroleum & Chemical Corporation, Beijing (CN); Beijing Research Institute of Chemical Industry, China Petroleum & Chemical Corporation, Beijing (CN)

( * ) Notice: Subject to any disclaimer, the term of this patent is extended or adjusted under 35 U.S.C. 154(b) by 454 days.

(21) Appl. No.: 14/064,244

(22) Filed: Oct. 28, 2013

(65) Prior Publication Data

US 2014/0121432 A1 May 1, 2014

(30) Foreign Application Priority Data

Oct. 29, 2012 (CN) .......................... 2012 1 0419841
Oct. 29, 2012 (CN) .......................... 2012 1 0420746
Oct. 29, 2012 (CN) .......................... 2012 1 0420748

(51) Int. Cl.
*C07C 4/04* (2006.01)
*B01J 3/00* (2006.01)
*C10G 9/36* (2006.01)

(52) U.S. Cl.
CPC .. *C07C 4/04* (2013.01); *B01J 3/00* (2013.01); *C10G 9/36* (2013.01); *C10G 2300/1088* (2013.01); *C10G 2300/1092* (2013.01)

(58) Field of Classification Search
CPC .................................... B01J 3/00; C07C 4/04
USPC ............ 585/648, 652; 208/130, 106, 78, 72
See application file for complete search history.

(56) References Cited

U.S. PATENT DOCUMENTS

| | | | |
|---|---|---|---|
| 3,617,493 A * | 11/1971 | Wirth | C10G 51/06 208/130 |
| 4,021,501 A * | 5/1977 | Dyer | C10G 9/00 208/130 |
| 4,492,624 A | 1/1985 | Johnson et al. | |
| 4,548,706 A | 10/1985 | Papadopoulos et al. | |
| 4,615,795 A * | 10/1986 | Woebcke | C10G 51/023 208/130 |
| 4,940,828 A | 7/1990 | Petterson et al. | |
| 5,542,262 A | 8/1996 | Park | |
| 7,339,087 B2 | 3/2008 | Cruijsberg et al. | |
| 2006/0089518 A1 | 4/2006 | Bouvart et al. | |
| 2007/0208207 A1 | 9/2007 | Powers | |
| 2007/0232845 A1 | 10/2007 | Baumgartner et al. | |
| 2007/0261991 A1 | 11/2007 | Beattie et al. | |
| 2009/0050530 A1 | 2/2009 | Spicer et al. | |
| 2009/0178956 A1 | 7/2009 | Devakottai | |
| 2010/0300936 A1 | 12/2010 | Stell et al. | |

FOREIGN PATENT DOCUMENTS

| | | |
|---|---|---|
| CN | 1050893 A | 4/1991 |
| CN | 1077978 C | 1/2002 |
| CN | 1501898 A | 6/2004 |
| CN | 101531917 A | 9/2009 |
| DE | 3708332 A1 | 9/1988 |
| DE | 4241144 A1 | 3/1994 |
| EP | 2 189 436 A1 | 5/2010 |
| GB | 571736 A | 9/1945 |
| GB | 1049046 | 11/1966 |
| WO | WO 2006/063201 A1 | 6/2006 |

OTHER PUBLICATIONS

Search Report and Written Opinion issued from the European Patent Office for the corresponding Belgian patent application No. BE 2013/00734, dated Jun. 18, 2015 (22 pages).
Dutch Search Report Aug. 20, 2014.
Thesis: Zhang, Lijun, *Study on Modeling of Thermal Cracking and Its Application*, dated Jun. 15, 2011.

* cited by examiner

*Primary Examiner* — Sharon Pregler
(74) *Attorney, Agent, or Firm* — Finnegan, Henderson, Farabow, Garrett & Dunner, LLP

(57) ABSTRACT

The present disclosure provides a steam cracking process, comprising heating a liquid feed stock in a convection section of a cracking furnace and subsequently conveying the material to a radiant section of the cracking furnace for cracking reaction therein, wherein a monoolefin-containing stream is conveyed to the cracking furnace for cracking reaction through at least one of modes A to C.

19 Claims, 4 Drawing Sheets

STEAM CRACKING PROCESSES

This application claims benefit of priority under 35 U.S.C. §119 to Chinese Patent Application Nos. CN 2012104198411, CN 201210420746.9, and CN 201210420748.8, filed Oct. 29, 2012, the contents of which are also incorporated herein by reference.

TECHNICAL FIELD

The present disclosure relates to a steam cracking process.

TECHNICAL BACKGROUND

Light olefins such as ethylene, propylene and butadiene are important basic raw materials in the petrochemical industry and are mainly produced by the cracking furnace steam cracking process at present. Statistics shows that about 99% of ethylene, more than 50% of propylene and more than 90% of butadiene in the world are produced by the above process.

A process unit based on the cracking furnace steam cracking process and the downstream cryogenic separation process as essential technologies is called an ethylene plant. A cracking furnace comprising a convection section and a radiant section is the key apparatus of an ethylene plant, wherein feed stocks and diluted steam are first separately heated in the convection section, and then mixed, vaporized and heated to an initial cracking temperature (i.e., a crossover temperature) before entering into the radiant section for cracking reaction. Generally, the radiant section of an industrial cracking furnace is provided with a plurality of furnace tubes of the same composition and configuration. A feed stock is fed into the furnace tubes, the outer ails of which are heated by heat released from liquid or gas fuel combustion. The heat is then transferred to the feed stock in the furnace tubes through the outer walls.

As is known to all, cracking is a process whereby carbon-carbon bonds in saturated petroleum hydrocarbons are broken down or dehydrogenated under high temperature into olefins and other products. The object of cracking is to produce ethylene and propylene, with side products such as butene, butadiene and other olefins and pyrolysis gasoline, diesel, fuel oil, etc.

Synthesized rubber and resin with butadiene as the monomer have been so rapidly developed in recent years that the prices of butadiene products are increasingly high and butadiene products have become important profit sources of ethylene plants. Different feed stocks lead to different butadiene yields. Gas feed stocks (lighter than C5 hydrocarbons) usually bring about a comparatively low butadiene yield, which for example is only about 4% in n-butane cracking products, while liquid feed stocks (such as naphtha, hydrogenated cracking residue, etc.) would result in a comparatively high yield of butadiene, which for example can be as high as 7% in hydrogenated cracking residue cracking products. Some of the olefins generally considered as incapable of serving as feed stocks may produce quiet high yield of butadiene, which for example can surprisingly reach as high as 18% in the catalytic cracking products of cis-butene. Therefore, the yield of butadiene can be expected to increase with addition of olefins such as cis-butene in the catalytic cracking furnace for cracking reaction.

The cracking portion of an ethylene plant usually comprises a plurality of liquid cracking furnaces and one gas cracking furnace. Feed stocks for the gas furnace are generally ethane, propane, C4 alkanes, etc., which are fed into the furnace in the gas phase and do not have to be vaporized in the convection section of the cracking furnace, so that the cracking furnace can be simply designed. Liquid cracking furnaces, on the other hand adopt naphtha, diesel, hydrogenated cracking residue, etc. as raw materials, which are fed into the furnaces in the liquid phase and thus need to be vaporized in the convection section of the cracking furnaces usually with complex structures.

Generally speaking, the convection section of a cracking furnace mainly functions in two aspects, for one thing, to preheat, vaporize and overheat the feed stock to the initial cracking temperature (the crossover temperature) and for another to recover the exhaust heat in the flue gas, so that the thermal efficiency of the furnace can be improved. Therefore, in view of different process requirements, the convection section normally employs different heat exchange arrangements, and mainly comprises a material preheating segment, a boiler feedwater preheating segment, a diluted steam overheating segment, a high pressure steam overheating segment and a hybrid heating segment. The convection section of the cracking furnace is continuously developed as technology develops. On the one hand, the number of the convection sections is increasingly larger. For example, in accordance with the amount of flue gas heat, the material preheating segment can be divided into the upper material preheating segment, mid-material preheating segment and lower material preheating segment. On the other hand, the feeding manner of diluted steam can be as diversified as comprising the one-off feeding manner and the secondary feeding manner based on different raw materials. These different feeding manners are adopted to prevent the raw material from being coked in the convection section. When liquid raw materials such as naphtha, diesel, hydrogenated cracking residue, etc. are used, a vaporization process exists in the convection section in the heating process, wherein if the raw material contains olefins, then at the beginning of the vaporization process, a high content of olefins in the gas phase would easily cause formation of coke, and when the vaporization process is to be ended, hydrocarbon components in the liquid phase would be so heavy that coke is also easily formed. In case severe coke is formed in the convection section of the cracking furnace, not only the heat transfer process would be seriously affected, but the pressure drop therein would also be rapidly increased, which would reduce the yield in the cracking furnace. When coke is accumulated to a certain limit, the cracking furnace will have to be shut down for mechanical decoking. In the prior art, the content of olefins in liquid feed stocks for cracking generally cannot be higher than 2 wt %. Once the content of olefins is too high, subsequent problems would be brought about, such as the formation of coke in the convection section of the cracking furnace and great decrease in the operation cycle of the cracking furnace, whereby causing maintenance shutdown of the cracking furnace.

Some embodiments are disclosed in the prior art for feeding various kinds of feed stocks into the convection section of a cracking furnace. For example, CN 1077978 A discloses a process for preparing ethylene by petroleum hydrocarbon steam cracking in the convection section. The process adopts the twice injection mode, i.e., primary steam injection at three points and secondary steam injection at one point, so that the cracking furnace is adapted to not only light materials but also heavy materials. Moreover, pipe lines are unnecessary to be replaced in the switch between raw materials. Nevertheless, the above patent application merely relates to improvement of steam injection modes, which does not influence the cracking yield or product quality in the whole cracking process.

CN 1501898 A discloses a process for cracking light feeding material in a cracking furnace for cracking heavy feeding material, comprising feeding part of the light material through an inlet of the convection section of the cracking furnace and feeding the rest light material into the convection section together with diluted gas. This process solves the problem of feeding light material into the cracking furnace when heavy material is replaced by light material, wherein an excessive pressure drop can be prevented when the light material passes through a preheating section.

US 2009/0178956 A1 discloses a process of reducing formation of coke of liquid feed stock in the convection section, wherein the partial pressure of the liquid material is reduced by feeding a gas phase when the liquid material is being preheated so as to improve the vaporization rate of the resulting mixture of the liquid material and the dilution steam and delay the formation of coke precursors of the liquid material, thus reducing or even eliminating formation of coke of the liquid material in the convection section.

Currently, steam cracking processes focus on how to enable the cracking furnace to be suitable for a variety of materials, for example from light to heavy materials, or on how to slow down or eliminate the formation of coke when heavy material is being used. In the prior art, there is limited disclosure relating to the process of feeding olefins (a monoolefin-containing stream) as part of the feed stock into the cracking furnace for steam cracking, not to mention eliminating formation of coke when olefins are injected into the cracking furnace as part of the feed stock.

Usually, the feed stock is preheated in the convection section of a cracking furnace before entering into the radiant section for cracking reaction, wherein the feed stock absorbs heat to so high a temperature that cracking reaction is generated to produce target products such as ethylene, propylene, butadiene, etc. At the outlet of the radiant section of the furnace, the cracked gases can react for a second time under high temperature to produce side products. Therefore, the high-temperature cracked gases need to be rapidly cooled at the outlet of the radiant section of the furnace to prevent too many secondary reactions to affect yield of the target products. For cooling of the cracked gases, both the direct quenching method and the indirect quenching method can be adopted, wherein the direct quenching method means directly contacting cryogens with the cracked gases to cool the gases rapidly, while the indirect quenching method means indirectly contacting cryogens with the cracked gases through a wall to cool the gases rapidly. The indirect quenching method is usually adopted in order to recover the heat of high-temperature cracked gases so as to improve the thermal efficiency of the cracking furnace and reduce the costs of the products, wherein a quench heat exchanger is used, i.e., a transfer line exchanger (TLE) is used for cooling the cracked gases rapidly and recover the heat to produce steam.

SUMMARY OF THE INVENTION

The present disclosure aims to solve the problem of formation of coke when olefins (a monoolefin-containing stream) are injected as part of the feed stock into the cracking furnace, so as to provide a new steam cracking process.

Therefore, the present disclosure provides a steam cracking process, comprising heating a liquid feed stock in a convection section of a cracking furnace and subsequently conveying the material to a radiant section of the cracking furnace for cracking reaction therein, wherein a monoolefin-containing stream is conveyed to the cracking furnace for cracking reaction through at least one of the following modes:

Mode A: mixing a first mixture with the liquid feed stock, heating the mixed resultant in the convection section, and then feeding it to the radiant section for cracking reaction;

Mode B: feeding the monoolefin-containing stream or the first mixture to an inlet of the radiant section, and mixing the same with material from the convection section; and Mode C: feeding the monoolefin-containing stream or the first mixture to an outlet of the radiant section, and mixing the same with products of a first cracking reaction for a second cracking reaction.

The monoolefin-containing stream is a hydrocarbon stream containing at least one selecting from a group consisting of ethylene, propylene, butene, pentene and hexene, the sum content of ethylene, propylene, butene, pentene and hexene accounting for more than 10% by weight of the hydrocarbon stream.

The first mixture is a mixture comprising the monoolefin-containing stream and at least one of steam and hydrogen.

Specifically, in Mode A of the present disclosure, the first mixture is mixed with the liquid feed stock inside or outside the convection section, preferably outside the convection section, before entering into a hybrid heating segment of the convection section. In Mode C according to the present disclosure, the outlet of the radiant section means an area adjacent the outlet in the radiant section.

It can be easily understood that in the above Modes B and C, the monoolefin-containing stream (or the monoolefin stream in the first mixture) is fed into the radiant section means that the stream is not heated together with the liquid feed stock in the convection section.

It can be also easily understood that in the present disclosure, the cracking reaction at least comprises a first cracking reaction and can optionally comprise a second cracking reaction. Moreover, one skilled in the art can easily understand that the cracking reaction occurring from an inlet to the inside of the radiant section is the first cracking section, while the cracking reaction occurring at an outlet of the radiant section is the second cracking reaction.

In one specific embodiment of Mode A, the first mixture enters into a hybrid heating segment of the convection section after being mixed with the liquid feed stock outside the convection section. Preferably, the first mixture is first heated in a diluted steam superheating segment of the convection section before being mixed with the liquid feed stock and then entering into the hybrid heating segment of the convection section.

In Mode A of the present disclosure, one specific embodiment is to mix the monoolefin-containing stream with steam. In heating the resulting feed stock mixture in the convection section of the cracking furnace, since the monoolefins in the feed stock mixture are fed together with steam, at the beginning of the vaporization of the feed stock mixture, steam would dilute the gas phase so as to reduce the content of monoolefins in the gas phase and further reduce or even prevent formation of coke in the beginning period of the vaporization. Besides, when the vaporization of the feed stock mixture is to be ended, steam is overheated and can promote rapid vaporization of the liquid feed stock, so that comparatively heavy components of the feed stock can be vaporized, thus achieving the object of reducing formation of coke when the vaporization is to be ended. Therefore, the process according to the present disclosure can alleviate the coking of monoolefins as feed stock in the convection section of the cracking furnace, so that the cracking furnace can be stably operated in a long term.

In Mode A according to the present disclosure, another specific embodiment is to mix the monoolefin-containing stream with hydrogen. Before being mixed with the liquid feed stock, hydrogen is added into the monoolefin-containing stream in the convection section of the cracking furnace, which is beneficial for slowing down the formation of coke of olefins.

In still another specific embodiment of Mode A according to the present disclosure, the monoolefin-containing material is mixed with steam and hydrogen. In this case, the formation of coke is more effectively slowed down.

In the prior art, it is known to one skilled in the art that cracking reaction is a strong endothermic reaction. If a small part of the feed stock can be directly injected to the outlet of the radiant section of the cracking furnace, the temperature of the cracked gases would be reduced as yield of the cracking products is increased, so that the high-temperature heat of the cracked gases can be fully utilized. Therefore, in another known process in the prior art with respect to the above Mode B and/or Mode C, a conventional liquid feed stock is injected to the outlet of the radiant section of a cracking furnace. However, the temperature at the outlet of the radiant section would be significantly reduced due to the injection of the liquid feed stock, so that a comparatively large number of liquid phase cracking products would be obtained during the cracking reaction at the outlet of the radiant section. As a result, the coking rate in a quenching apparatus would be increased, which would further affect the cycle of operation of the whole cracking apparatus. Consequently, according to the solution of Mode C of the present disclosure, in the steam cracking process, cracking reaction would be generated between olefins (the monoolefin-containing stream) and products of a first cracking reaction in the radiant section after being mixed. The cracking temperature of an olefin is comparatively low and no liquid product would be obtained in the cracking of an olefin, so that the high-temperature heat of the cracking reaction products in the radiant section can be effectively utilized, the product yield can be increased and the formation of coke in the quench apparatus can be slowed down.

In Mode B according to the present disclosure, the monoolefin-containing stream is fed into the cracking apparatus from the inlet of the radiant section. Therefore, the addition of olefins would not bring about coke in the convection section of the cracking furnace. In the radiant section of the cracking furnace, olefins would co-crack with the liquid feed stock.

In Mode C according to the present disclosure, the monoolefin-containing stream is fed into the cracking apparatus from the outlet of the radiant section. Therefore, the addition of olefins would not bring about formation of coke in the convection section of the cracking furnace, either. At the outlet of the radiant section of the cracking furnace, olefins would co-crack with the products of the first cracking reaction from the radiant section.

In one specific embodiment, the monoolefin-containing stream of the present disclosure is a hydrocarbon stream with the sum content of ethylene, propylene, butene, pentene and hexene accounting for more than 30% by weight of the hydrocarbon stream, preferably a hydrocarbon stream with the sum content of butene, pentene and hexene accounting for more than 50% by weight of the hydrocarbon stream, and more preferably a hydrocarbon stream with the sum content of 1-butene and 2-butene accounting for more that 50% by weight of the hydrocarbon stream. Through experiments, the inventor of the present disclosure finds that when the monoolefin-containing material added to the cracking furnace comprises a certain amount of 1-butene and 2-butene, the monoolefin-containing material would co-crack with the liquid feed stock and/or the products of the first cracking reaction generated in the radiant section, so that a relatively high yield of butadiene can be obtained.

Preferably, in Mode A, a mixture of the monoolefin-containing stream and steam is preheated to a temperature in a range from 480 to 560° C., preferably in a range from 500 to 540° C. in the convection section before being mixed with the liquid feed stock. In the above solution, more preferably, the liquid feed stock is preheated to a temperature in a range from 230 to 300° C., preferably from 250 to 280° C. in the convection section before being mixed with the mixture of the monoolefin-containing stream and steam.

Preferably, in Mode A, the dosage ratio of the monoolefin-containing stream to steam ranges from 1:1 to 1:30 by weight, and/or the dosage ratio of the monoolefin-containing stream to the liquid feed stock ranges from 0.001:1 to 0.2:1 by weight.

In one specific embodiment of the present disclosure, in Modes B and C, the monoolefin-containing stream, hydrogen, steam and any mixtures thereof are all separately and optionally preheated to a temperature in a range from 120 to 660° C., preferably 150 to 620° C. in the convection section.

In one specific embodiment, in Modes B and C, a separate monoolefin-containing stream is used and preheated to a temperature ranging from 120 to 250° C., preferably 150 to 200° C. before entering into the radiant section. In one specific embodiment, the monoolefin-containing stream can be preheated in a heating apparatus such as an evaporator instead of being preheated in the convection section, wherein it can be easily understood the separate monoolefin-containing stream means that the monoolefin-containing stream is not used by being mixed with steam or hydrogen In another specific embodiment, in Modes B and C, the first mixture is the mixture of the monoolefin-containing stream and steam, and the preheated temperature thereof before entering into the radiant section is in a range from 500 to 660° C., preferably from 540 to 620° C.

Specifically, in Mode B, the dosage ratio of the monoolefin-containing stream to the liquid feed stock ranges from 0.001:1 to 0.5:1, preferably from 0.01:1 to 0.4:1 by mass; and in Mode C, the dosage ratio of the monoolefin-containing stream to the liquid feed stock ranges from 0.001:1 to 0.2:1, preferably from 0.01:1 to 0.1:1 by mass.

Preferably, in Modes B and C according to the present disclosure, in the first mixture, the mass ratio of the monoolefin-containing stream to hydrogen ranges from 50:1 to 1,000:1, preferably from 80:1 to 800:1, and/or in the first mixture the mass ratio of the monoolefin-containing stream to steam ranges from 0.1:1 to 10:1, preferably from 0.2:1 to 3:1.

In the present disclosure, conditions of the first cracking reaction comprise an initial cracking temperature in a range from 560 to 660° C., preferably in a range from 580 to 640° C.; an outlet temperature of the radiant section in a range from 780 to 850° C., preferably from 790 to 840° C.; and a reaction time in a range from 0.1 to 0.5 s, preferably from 0.2 to 0.3 s.

Preferably, the liquid feed stock according to the present disclosure comprises naphtha and/or hydrogenated cracking residue.

In the present disclosure, the cracking furnace is not a catalytic cracking furnace, and the cracking furnace contains no catalysts for cracking.

BRIEF DESCRIPTION OF DRAWINGS

The drawings which constitute part of this disclosure are provided for further understanding of the present disclosure and for explaining the present disclosure together with the specific embodiments without limiting the present disclosure in any manner.

DETAILED DESCRIPTION OF EMBODIMENTS

In the present disclosure, unless otherwise indicated, the terms "upper" and "lower" usually mean an upper or lower portion with reference to the drawings, while "inside" and "outside" refer to inside or outside of corresponding component.

Figure 2:
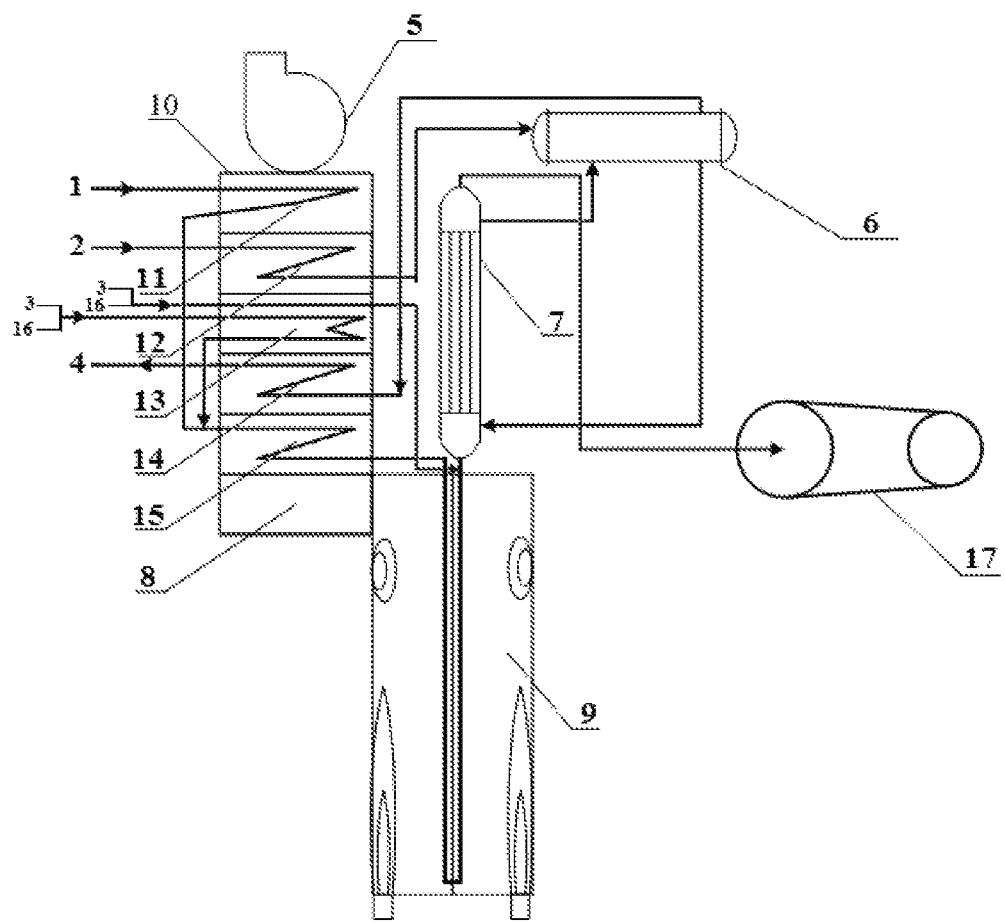
FIG. 2 schematically shows the cracking apparatus and the direction of material flow according to Example 1 of the present disclosure.

FIG. 2 schematically shows the cracking apparatus comprising a cracking furnace and the direction of material flow according to Example 1 of the present disclosure. The cracking apparatus comprises a cracking furnace, a transfer line exchange 7, a steam drum 6, a blower 5 and a cracked gas manifold 17. The cracking furnace comprises a convection section 10 and a radiant section 9. The feed stock enters into the radiant section 9 via the convection section 10, wherein the feed stock which has been preheated in the convection section 10 is further heated in the radiant section 9 for cracking reaction under heat released from the combustion of liquid or gas fuel therein. At an outlet of the radiant section 9, the products of the cracking reaction are mixed with a monoolefin-containing stream or a first mixture (comprising a monoolefin-containing stream and at least one of steam and hydrogen) for a second cracking reaction under the temperature of the mixed resultant per se. Subsequently, the resulting reaction products are injected into the transfer line exchange 7 to be cooled and separated into cracked gases and steam. The steam then enters into the steam drum 6 for gas-liquid separation. The separated high-pressure steam can enter into the convection section to be heated therein to obtain super high pressure steam, while the separated water can be used as the cooling water of the transfer line exchange 7. The cracked gases enter into subsequent separation devices via the cracked gas manifold 17 for separation of the target products. High-temperature flue gas generated by combustion in the radiant section 9 enters into the convection section 10 via a flue gas across section 8. The transfer line exchange 7 is preferably a quench heat exchanger, i.e., an indirect transfer line exchange.

In order to fully utilize the heat of the high-temperature flue gas from the radiant section 9, the convection section 10 of the cracking furnace is usually provided with a plurality of segments for recovering heat. Generally, the convection section 10 can be provided with one or more of a material preheating segment 11 for preheating the feed stock, a boiler feedwater preheating segment 12 for heating the boiler feedwater fed to the steam drum 6, a diluted steam overheating segment 13 for preheating diluted steam (such as water steam), a super high pressure steam overheating segment 14 for heating high pressure steam from the steam drum 6 to obtain super high pressure steam and a hybrid heating segment 15 for heating the feed stock to the crossover temperature. The above mentioned segments can be provided in accordance with actual requirements. For example, when the feed stock needs to be preheated before being mixed with other materials (such as diluted steam), the material preheating segment 11 is necessary. On the contrary, the material preheating segment 11 will be unnecessary if the feed stock doesn't need to be preheated before being mixed with other materials.

Furthermore, in accordance with actually requirements, the convection section 10 can be provided with one or a plurality of material heating segments 11. In one embodiment, when the feed stock is injected in a plurality of streams and each of the streams needs to be preheated before being mixed with each other, then the convection section 10 needs to be provided with a plurality of material preheating segments 11, each of which can preheat one stream. In another embodiment, when the feed stock needs to be preheated to a relatively high temperature and one material preheating segment cannot preheat the feed stock to the target temperature, then the convection section 10 will need to be provided with a plurality of the material preheating segments 11 so as to preheat the feed stock for a plurality of times.

According to actual production requirements, in order to obtain super high pressure steam of certain temperature and pressure, the convection section 10 can be provided with one or a plurality of high pressure steam overheating segments 14.

According to actual production requirements, in order to heat the feed stock to the crossover temperature so as to reduce load of the radiant section, the convection section 10 can be provided with one or a plurality of the hybrid heating segments.

In the cracking furnace, when the convection section 10 is provided with more than two segments chosen from the material preheating segment 11, the boiler feedwater preheating segment 12, the diluted steam overheating segment 13, the super high pressure steam overheating segment 14 and the hybrid heating segment 15, the position of each of the above segments can be determined according to actual requirements. When the medium in one certain segment needs to be intensively heated, i.e., to be heated to a high temperature, this segment can be arranged adjacent to the crossover section 8, where the temperature of the flue gas is relatively high; when the medium in this segment needs to be heated with lower intensity, i.e., to be heated to a low temperature, this segment can be arranged away from the crossover section 8, since the temperature of the flue gas becomes lower as flowing away from the crossover section 8. For example, in one embodiment as shown in FIG. 2, in the convection section 10, along the flow direction of high-temperature flue gas, the hybrid heating segment 15, the super high pressure steam overheating segment 14, the diluted steam overheating segment 13, the boiler feedwater preheating segment 12 and the material preheating segment 11 are successively provided.

In one specific steam cracking process according to FIG. 2 of the present disclosure, the steam cracking process is carried out in a cracking apparatus, which comprises a cracking furnace and a transfer line exchange 7, the cracking furnace further comprising a convection section 10 and a radiant section 9. The process includes the following steps:

Step (1): a liquid feed stock 1 is mixed with a mixture comprising a monoolefin-containing stream 16 and a steam 3 and the resulting feed stock mixture is heated in the convection section 10, vaporized and heated to a crossover temperature, after which the vaporized feed stock mixture is fed into the radiant section 9 for a first cracking reaction to obtain products of the first cracking reaction;

Step (2): the monoolefin-containing stream or the first mixture is mixed with the products of the first cracking reaction at an outlet of the radiant section 9 for a second cracking reaction to obtain products of the second cracking reaction, which are then injected into the transfer line exchange 7 to be cooled and separated.

In the present disclosure, said term "preheating" can be exchangeably used as the term "heating", both indicating heating the material to be cracked to a temperature lower than the first cracking reaction temperature.

In a preferred embodiment, the process further comprises: in Step (1), preheating the liquid feed stock in the convection section 10 before mixing the same with the mixture comprising monoolefin-containing stream and steam. According to the embodiment, coking can be further relieved. Preferably, the temperature of the liquid feed stock after being preheated in the convection section 10 is in a range from 230 to 300° C., more preferably from 250 to 280° C.

In another embodiment, the process further comprises, in Step (1), preheating the mixture comprising the monoolefin-containing stream and steam in the convection section 10 before mixing the same with the liquid feed stock. The temperature of the mixture comprising the monoolefin-containing stream and steam after being preheated in the convection section 10 is preferably in a range from 480 to 560° C., more preferably from 500 to 540° C.

In Step (1), the dosage ratio of the liquid feed stock to steam is in a range from 1:1 to 4:1, preferably from 1.5:1 to 2.5:1 by weight.

In Step (1), the dosage ratio of the monoolefin-containing stream to steam is in a range from 1:1 to 1:30, preferably from 1:10 to 1:20 by weight.

In Step (1), the first cracking can be implemented under conventional cracking conditions. Preferably, the conditions for the first cracking include: the crossover temperature in a range from 560 to 660° C., preferably 580 to 640° C.; the temperature at the outlet of the radiant section in a range from 780 to 850° C., preferably 790 to 840° C.; and the reaction time (the residence time of the feed stock mixture in the radiant section 9) in a range from 0.1 to 0.5 s, preferably 0.2 to 0.3 s.

In still another preferred embodiment, the process further comprises: preheating the monoolefin-containing stream or the first mixture in the convection section 10 before mixing the same with the products of the first cracking reaction. According to the preferred embodiment, a great decrease of the temperature at the outlet of the radiant section can be avoided, so that olefins can be ensured to be fully cracked. Preferably, the temperature of the monoolefin-containing stream or the first mixture after being preheated in the convection section 10 is in a range from 120 to 660° C., preferably 150 to 620° C. In the above embodiments, the preheating steps in the convection section 10 are respectively carried out in different segments of the convection section 10. Specifically, the liquid feed stock is preheated in the material preheating segment 11 of the convection section 10, while the monoolefin-containing stream is preheated in the diluted steam superheating segment 13 of the convection section 10.

In a further preferred embodiment as shown in FIG. 2, in the convection section 10, the liquid feed stock 1 is preheated in the material preheating segment 11, while at the same time the mixture comprising the monoolefin-containing stream 16 and the steam 3 is preheated in the diluted steam superheating segment 13, after which the liquid feed stock which has been preheated in the material preheating segment 11 and the mixture comprising the monoolefin-containing stream and the steam which has been preheated in the diluted steam superheating segment 13 are mixed to obtain a feed stock mixture. The feed stock mixture is subsequently heated in the hybrid heating segment 15 to the crossover temperature and then injected into the radiant section 9 for cracking reaction (i.e., the first cracking reaction). Meanwhile, another monoolefin-containing stream 16 or mixture comprising the monoolefin-containing stream 16 and steam 3 is preheated in the diluted steam superheating segment 13 to obtain a preheated stream containing olefins. Subsequently, the preheated olefin-containing stream is mixed with the cracking products (i.e., products of the first cracking reaction) at the outlet of the radiant section 9 and cracked under the temperature of the obtained mixture per se (i.e., the second cracking reaction). Afterwards, the final cracking products (i.e., products of the second cracking reaction) are injected into the transfer line exchange 7 to be cooled and separated.

In addition, in the above preferred embodiment, in order to fully utilize the heat of high temperature flue gas in the convection section 10, boiler feedwater 2 can be optionally heated through the boiler feedwater preheating segment 12 and high-pressure steam 4 from the steam drum 6 can be heated in the super high pressure steam overheating segment 14 to obtain super high pressure steam. In the convection section 10 of the preferred embodiment, preferably, the hybrid heating segment 15, the high pressure steam overheating segment 14, the diluted steam superheating segment 13, the boiler feedwater preheating segment 12 and the material preheating segment 11 are successively provided along the flow direction of the high-temperature flue gas.

In Step (2) of the process provided in the present disclosure, the first mixture preferably is a mixture comprising the monoolefin-containing stream and steam. More preferably, the dosage ratio of the monoolefin-containing stream to steam is in a range from 0.1:1 to 10:1, preferably 0.5:1 to 2:1 by weight.

In Step (2) of the process provided in the present disclosure, the dosage ratio of the monoolefin-containing stream to the liquid feed stock is in a range from 0.001:1 to 0.2:1, preferably 0.01:1 to 0.1:1 by weight.

In Step (2) of the process provided in the present disclosure, the second cracking reaction is carried out at the temperature of the mixture of the cracking reaction products in the radiant section 9 (products of the first cracking reaction) and the monoolefin-containing stream or the first mixture. The reaction time of the second cracking reaction is relatively short, which can be shorter than 0.1 s, preferably in a range from 0.001 to 0.05 s.

In the process according to the present disclosure, the monoolefin-containing streams in Steps (1) and (2) can be the same or different.

Figure 3:
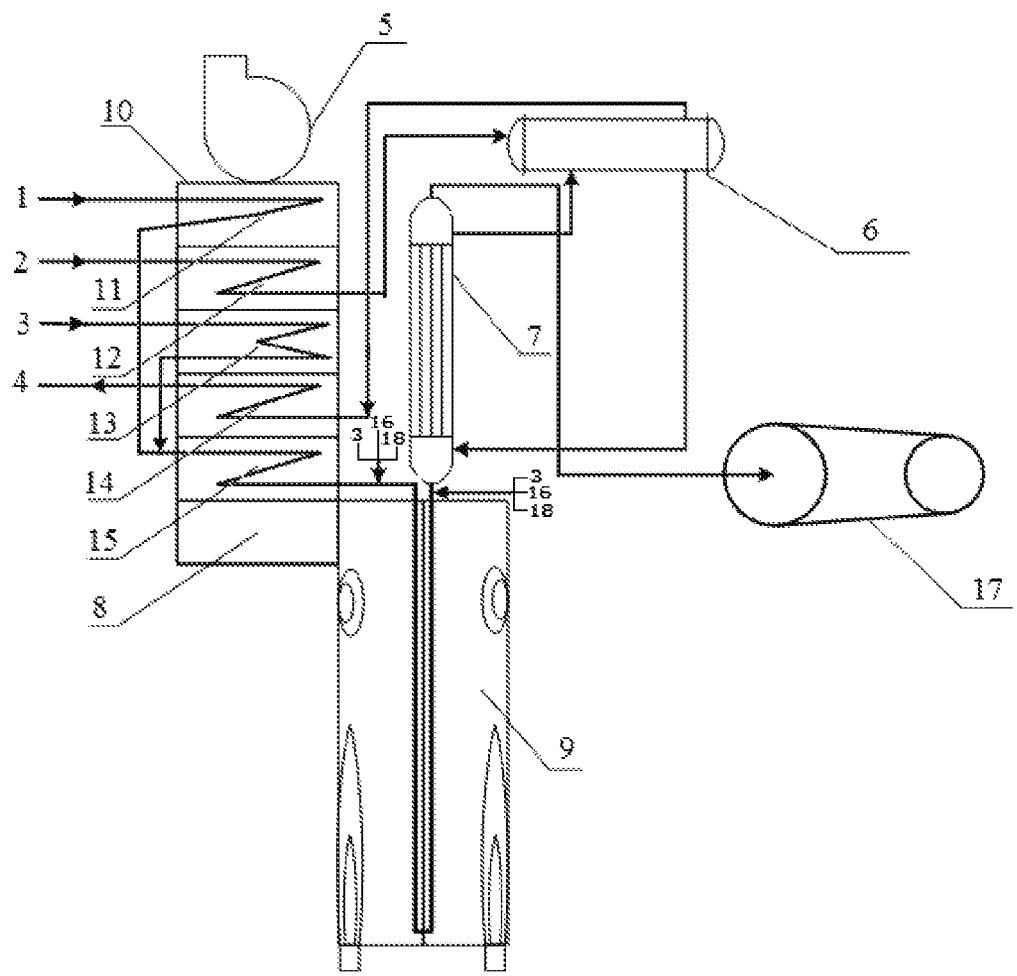
FIG. 3 schematically shows the cracking apparatus and the direction of material flow according to Example 3 of the present disclosure.

Another specific embodiment according to the present disclosure is as shown in FIG. 3.

The steam cracking process according to FIG. 3 is implemented in a cracking apparatus, comprising a cracking furnace, a transfer line exchange 7 and a heating apparatus (not shown in the drawing). The cracking furnace comprises a convection section 10 and a radiant section 9. Said process comprises: mixing a liquid feed stock with steam and heating the resulting feed stock mixture in the convection section 10 to a crossover temperature and feeding the feed stock mixture into the radiant section 9 for cracking reaction. The obtained cracking reaction products are injected into the transfer line exchange 7 to be cooled and separated, wherein the process further comprises at least one of the flowing procedures:

Procedure (a): the monoolefin-containing stream in the heating apparatus is heated and before the heated feed stock mixture is fed into the radiant section, it is mixed with the first mixture, the first mixture being a mixture of the heated monoolefin-containing stream and hydrogen or a mixture of the heated monoolefin-containing stream and hydrogen and steam.

Procedure (b): the monoolefin-containing stream heated in the heating apparatus, and before the cracking reaction products are injected into the transfer line exchange, they are contacted with the first mixture for reaction, said first mixture being a mixture of the heated monoolefin-containing stream and hydrogen or a mixture of the heated monoolefin-containing stream and hydrogen and steam.

In Procedure (a) of the process according to the present disclosure, the first mixture is added into the inlet of the radiant section, while in Procedure (b), the first mixture is added into the outlet of the radiant section 9. In the first mixture, the monoolefin-containing stream is preheated by the heating apparatus.

In the process according to the present disclosure, in Procedures (a) and (b), the temperatures of the monoolefin-containing streams after being heated in the heating apparatus can respectively be in a range from 120 to 250° C., preferably 150 to 200° C. The heating apparatus for heating the monoolefin-containing stream can be various kinds of conventional heating apparatuses, such as an evaporator. Under preferable conditions, the monoolefin-containing stream is injected into the evaporator for vaporization. The vaporized monoolefin-containing stream is then mixed with hydrogen and steam can be optionally added, wherein the resulting mixture is injected into the inlet and/or outlet of the radiant section 9.

When the process of the present disclosure simultaneously comprises Procedures (a) and (b), the monoolefin-containing streams in Procedures (a) and (b) can be heated in the same heating apparatus.

In a preferred embodiment, the steam cracking process further comprises: before the liquid feed stock is mixed with steam, the liquid feed stock is preheated in the convection section 10. The preferred embodiment can relieve coking. Preferably, the temperature of the liquid feed stock after being preheated in the convection section 10 is in a range from 120 to 300° C., preferably 150 to 250° C.

In the present disclosure, when the steam cracking process comprises Procedure (a), the convection section 10 is preferably provided with a material preheating segment 11, a diluted steam superheating segment 13 and a hybrid heating segment 15. The steam cracking process preferably comprises:

Step (1): the liquid feed stock is preheated in the material preheating segment 11;

Step (2): steam is preheated in the diluted steam superheating segment 13;

Step (3): the preheated liquid feed stock obtained in Step (1) is mixed with the preheated steam obtained in Step (2) and the resulting feed stock mixture is heated in the hybrid heating segment 15 so as to be vaporized and heated to the crossover temperature;

Step (4): the monoolefin-containing stream is heated in the heating apparatus before being mixed with hydrogen and the mixed resultant is optionally added with steam to obtain a first mixture;

Step (5): the vaporized feed stock mixture obtained in Step (3) is mixed with the first mixture obtained in Step (4) and the mixed resultant is added into the radiant section 9 for cracking reaction; and Step (6): the cracking products obtained in Step (5) are injected into the transfer line exchange 7 to be cooled and separated.

In the above embodiment, there is no special restriction on the sequence of Step (1), Step (2) and Step (4). Preferably, Step (1), Step (2) and Step (4) are carried out simultaneously.

In the present disclosure, when the steam cracking process comprises Procedure (b), the convection section 10 is preferably provided with the material preheating segment 11, the diluted steam superheating segment 13 and the hybrid heating segment 15. The steam cracking process preferably comprises:

Step (1): the liquid feed stock is preheated in the material preheating segment 11;

Step (2): steam is preheated in the diluted steam superheating segment 13;

Step (3): the preheated liquid feed stock obtained in Step (1) and the preheated steam obtained in Step (2) are mixed and the resulting feed stock mixture is heated in the hybrid heating segment 15 so as to be vaporized and heated to the crossover temperature;

Step (4): the vaporized feed stock mixture obtained in Step (3) is added into the radiant section 9 for cracking reaction;

Step (5): the monoolefin-containing stream heated in the heating apparatus before being mixed with hydrogen and the mixed resultant is optionally added with steam to obtain a first mixture; and Step (6): the cracking reaction products obtained in Step (4) are contacted with the first mixture obtained in Step (5) and the resulting products are injected into the transfer line exchange 7 to be cooled and separated.

In the above embodiment, there is no special restriction on the sequence of Step (1), Step (2) and Step (5). Preferably, Step (1), Step (2) and Step (5) are carried out simultaneously.

In a preferred embodiment, the steam cracking process simultaneously comprises Procedures (a) and (b), when the convection section 10 is preferably provided with the material preheating segment 11, the diluted steam superheating segment 13 and the hybrid heating segment 15. The steam cracking process preferably comprises:

Step (1): the liquid feed stock is preheated in the material preheating segment 11;

Step (2): steam is preheated in the diluted steam superheating segment 13;

Step (3): the preheated liquid feed stock obtained in Step (1) is mixed with the preheated steam obtained in Step (2) and the resulting feed stock mixture is heated in the hybrid heating segment 15 so as to be vaporized and heated to the crossover temperature;

Step (4): monoolefin-containing stream is heated in the heating apparatus before being mixed with hydrogen and the mixed resultant is optionally added with vapor to obtain a first mixture;

Step (5): the vaporized feed stock mixture obtained in Step (3) is mixed with part of the first mixture obtained in Step (4) and the mixed resultant is added into the radiant section 9 for cracking reaction; and Step (6): the cracking products obtained from Step (5) are contacted and reacted with another part of the first mixture obtained in Step (4) and the resulting products are injected into the transfer line exchange 7 to be cooled and separated.

In the above preferred embodiment, there is no strict limitation on the sequence of Step (1), Step (2) and Step (4). Preferably, Step (1), Step (2) and Step (4) are carried out simultaneously.

In the above preferred embodiment, specifically as shown in FIG. 3, in the convection section 10, the liquid feed stock 1 is preheated in the material preheating segment 11 and steam 3 is simultaneously preheated in the diluted steam superheating segment 13. Subsequently, the liquid feed stock preheated in the material preheating segment 11 and the steam 3 preheated in the diluted steam superheating segment 13 are mixed to obtain the feed stock mixture. Afterwards, the feed stock mixture is heated in the hybrid heating segment 15 to the crossover temperature and is mixed with a stream of the first mixture (i.e., the mixture comprising the monoolefin-containing stream heated by the heating apparatus and hydrogen or the mixture comprising the heated monoolefin-containing stream and hydrogen and steam). The resulting mixture is then injected into the radiant section 9 for cracking reaction. Next, the cracking reaction products contacted and reacted with another stream of the first mixture (i.e., the mixture comprising the monoolefin-containing stream heated by the heating apparatus and hydrogen or the mixture comprising the heated monoolefin-containing stream and hydrogen and steam) and the resulting reaction products are then injected into the transfer line exchange 7 to be cooled and separated.

Additionally, in the above embodiment, in order to fully utilize the heat in the high-temperature flue gas in the convection 10, the boiler feedwater 2 can be optionally heated in the material preheating segment 12 and the high-pressure steam 4 from the steam drum 6 can be heated to obtain high pressure superheated steam. Under this condition, in the convection section 10, preferably the hybrid heating segment 15, the high pressure steam overheating segment 14, the diluted steam superheating segment 13, boiler feedwater preheating segment 12 and the material preheating segment 11 are successively provided along the flow direction of the high-temperature flue gas.

In the process provided by the present disclosure, in mixing the liquid feed stock and steam, the dosage ratio of the liquid feed stock to the steam is in a range from 1:1 to 4:1, preferably from 1.5:1 to 2.5:1 by weight.

In Procedure (a), the dosage ratio of the monoolefin-containing stream to the liquid feed stock can be in a range from 0.001:1 to 0.5:1, preferably 0.01:1 to 0.4:1 by weight; the dosage ratio of the monoolefin-containing stream to hydrogen can be in a range from 50:1 to 1,000:1, preferably 80:1 to 800:1 by weight; and the dosage ratio of steam to the monoolefin-containing stream can be in a range from 0:1 to 5:1, preferably 0.1:1 to 3:1 by weight.

In Procedure (b), the dosage ratio of the monoolefin-containing stream to the liquid feed stock can be in a range from 0.001:1 to 0.2:1, preferably 0.01:1 to 0.1:1 by weight; the dosage ratio of the monoolefin-containing stream to hydrogen can be in a range from 50:1 to 1,000:1, preferably 80:1 to 800:1 by weight; and the dosage ratio of steam to the monoolefin-containing stream can be in a range from 0:1 to 5:1, preferably 0.1:1 to 3:1 by weight.

In the process according to the present disclosure, the cracking reaction in the radiant section 9 can be carried out under conventional cracking conditions. In preferred embodiments, the cracking conditions include: the crossover temperature being in a range from 560 to 660° C., preferably 580 to 640° C.; the temperature at the outlet of the radiant section being in a range from 780 to 850° C., preferably 790 to 840° C.; and the reaction time (i.e., the residence time of reaction material in the radiant section) in a range from 0.1 to 0.5 s, preferably 0.2 to 0.3 s.

In Procedure (b), the contacting time between the cracking reaction products from the radiant section 9 and the first mixture is relatively short, which can be shorter than 0.1 s, preferably in a range from 0.001 to 0.05 s. The contacting reaction time refers to the time period that the cracking reaction products from the radiant section 9 are contacted and reacted with the first mixture at the outlet of the radiant section 9 before entering into the transfer line exchange 7.

In the process according to the present disclosure, in Procedures (a) and (b), the monoolefin-containing streams can be the same or different.

In the following, the present disclosure will be further explained with reference to examples.

Example 1

This example is used to explain the steam cracking process provided in the present disclosure.

The cracking apparatus as shown in FIG. 2 is adopted for the cracking reaction. The specific process comprises:

Naphtha 1 of 60° C. (see Table 1 for the corresponding parameters) is preheated in the material preheating segment 11, and simultaneously a first stream composed of steam 3 and a monoolefin-containing (mixed C4 olefins) stream 16 with the composition as shown in Table 2 is preheated in the diluted steam superheating segment 13. After that, the preheated naphtha and the preheated first stream are mixed and the resulting feed stock mixture is heated in the hybrid heating segment 15 before entering into the radiant section 9 for cracking reaction. In addition, a second stream composed of steam 3 and mixed C4 olefins 16 with the composition as shown in Table 2 is preheated in the diluted steam superheating segment 13 to obtain a first mixture (the monoolefin-containing stream). At the outlet of the radiant section 9, the preheated second stream is mixed and reacted with the cracking reaction products in the radiant section 9. The resulting final cracking reaction products are injected into the transfer line exchange 7 to be cooled and separated to obtain a high-pressure steam and cracked gases, which are fed into the subsequent separation devices via the cracked gas main pipe 17. The feeding rate of the naphtha 1 is 43,130 kg/h, and in the first stream the injection rate of steam is 22,700 kg/h and the feeding rate of the mixed C4 olefins is 2,270 kg/h. In the second stream, the injection rate of steam is 2,270 kg/h and the feeding rate of the mixed C4 olefins is 1,362 kg/h. The temperatures of the preheated first and second streams are respectively 530° C. and 600° C. The crossover temperature (XOT) is 590° C. and the temperature at the outlet of the cracking furnace (COT) is 830° C. The cracking reaction time in the radiant section 9 is 0.24 s. Other process parameters of the cracking furnace and transfer line exchange 7 are listed in Table 3. The cracked gases are separated and analyzed and the composition thereof is shown as in Table 4.

TABLE 1

| | | |
|---|---|---|
| d15.6 | | 0.7090 |
| BMCI | | 9.0854 |
| Average molecular weight | | 100.89 |
| Hydrogen content (wt %) | | 15.4743 |
| PONA (wt %) | Normal-paraffin | 33.14 |
| | Isoparaffin | 36.00 |
| | Naphthene | 21.64 |
| | Olefin | 0.14 |
| | Aromatics | 9.07 |
| | Total | 100.00 |
| Boiling range (° C.) | Initial boiling point | 31.90 |
| | 10% | 54.20 |
| | 20% | 64.20 |
| | 30% | 73.60 |
| | 40% | 83.60 |
| | 50% | 95.50 |
| | 60% | 109.10 |
| | 70% | 123.60 |
| | 80% | 139.40 |
| | 90% | 157.50 |
| | 95% | 168.40 |
| | Final boiling point | 176.10 |

TABLE 2

| Composition | Content (wt %) | Composition | Content (wt %) |
|---|---|---|---|
| $C_3H_8$ | 0.07 | $i\text{-}C_4H_8$ | 3.96 |
| $C_3H_6$ | 0.10 | $t\text{-}C_4H_8$ | 40.83 |
| Propadiene | 0.01 | $c\text{-}C_4H_8$ | 18.18 |
| $i\text{-}C_4H_{10}$ | 2.78 | $1,3\text{-}C_4H_6$ | 0.10 |
| $n\text{-}C_4H_{10}$ | 24.29 | $C_5++$ | 0.13 |
| $1\text{-}C_4H_8$ | 9.52 | $C_6H_6$ | 0.02 |

Total: 100 wt %

TABLE 3

| | Flow (kg/h) | Temperature (° C.) | | Pressure (kPa-g) | |
|---|---|---|---|---|---|
| Feed stock Operational stage | Initial stage to final stage | Initial stage | Final stage | Initial stage | Final stage |
| Inlet of the material preheating segment | 43,130 | 60 | 60 | 511.6 | 542.3 |
| Outlet of the material preheating segment | | 184 | 188 | 495.7 | 513.5 |
| Inlet of the hybrid heating segment | 68,100 | 274 | 296 | 495.7 | 513.5 |
| Outlet of the hybrid heating segment | | 590 | 605 | 384.8 | 389.6 |
| Inlet of the transfer line exchange | 71,732 | 820 | 824 | 80.2 | 89.7 |
| Outlet of the transfer line exchange | | 397 | 450 | 64.8 | 64.8 |

TABLE 4

| Composition | Content (wt %) |
|---|---|
| Hydrogen | 0.88 |
| Methane | 11.82 |
| Ethane | 3.15 |
| Ethylene | 27.63 |
| Acetylene | 0.33 |
| Propane | 0.46 |
| Propylene | 16.98 |
| Methyl acetylene | 0.32 |
| Propadiene | 0.25 |
| Iso-butane | 0.01 |
| N-butane | 0.34 |
| Butene-1 | 2.11 |
| Isobutene | 2.74 |
| Trans-butene | 1.00 |
| Cis-butene | 1.52 |
| Butadiene | 5.88 |
| Others | 24.58 |
| Total | 100.00 |

Comparative Example 1

Figure 1:
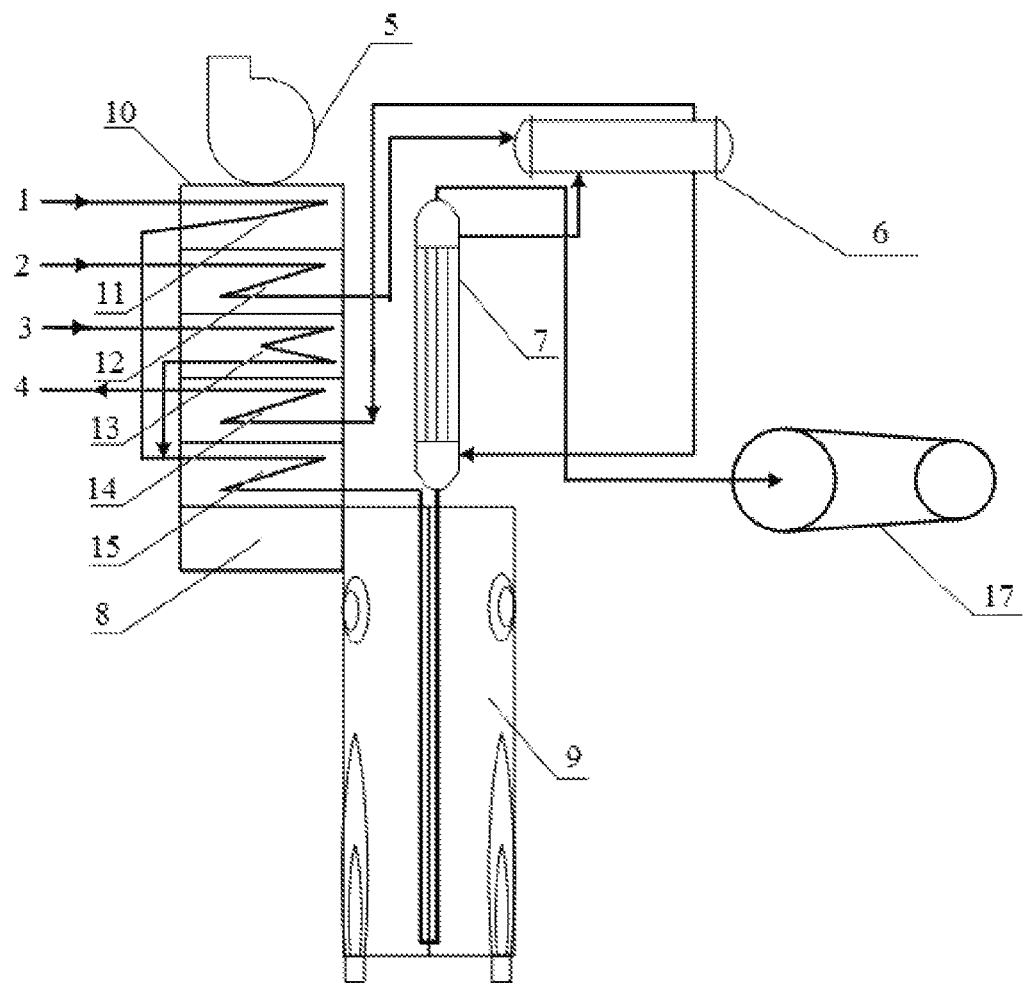
FIG. 1 schematically shows a prior art cracking apparatus comprising a cracking furnace and a transfer line exchange and the direction of material flow therein.

The steam cracking process is carried out according to the process as provided in Example 1 except that as shown in FIG. 1, the mixed C4 olefins 16 are not injected into the first stream or the second stream and that the feeding rate of naphtha is 45,400 kg/h, wherein other process parameters of the cracking furnace and transfer line exchange 7 are listed in Table 5, and the cracked gases are separated and analyzed and the composition thereof is shown as in Table 6.

TABLE 5

| | Flow (kg/h) | Temperature (° C.) | | Pressure (kPa-g) | |
|---|---|---|---|---|---|
| Feed stock Operational stage | Initial stage to final stage | Initial stage | Final stage | Initial stage | Final stage |
| Inlet of the material preheating segment | 45,400 | 60 | 60 | 511.6 | 542.3 |
| Outlet of the material preheating segment | | 182 | 187 | 496.5 | 512.3 |
| Inlet of the hybrid heating segment | 68,100 | 274 | 296 | 496.5 | 512.3 |
| Outlet of the hybrid heating segment | | 590 | 605 | 384.8 | 389.6 |
| Inlet of the transfer line exchange | 68,100 | 825 | 829 | 78.6 | 88.6 |
| Outlet of the transfer line exchange | | 405 | 463 | 64.8 | 64.8 |

TABLE 6

| Composition | Content (wt %) |
|---|---|
| Hydrogen | 0.81 |
| Methane | 11.79 |
| Ethane | 3.38 |
| Ethylene | 29.50 |
| Acetylene | 0.33 |
| Propane | 0.50 |
| Propylene | 16.94 |
| Methyl acetylene | 0.32 |
| Propadiene | 0.24 |
| Iso-butane | 0.04 |
| N-butane | 0.37 |
| Butene-1 | 2.11 |
| Isobutene | 2.93 |
| Trans-butene | 0.00 |
| Cis-butene | 0.51 |
| Butadiene | 4.84 |
| Others | 25.39 |
| Total | 100.00 |

The data in Tables 4 and 6 indicate that the yields of butadiene in Example 1 and Comparative Example 1 are respectively 5.88 wt % and 4.84 wt %. That is, by introducing mixed C4 olefins into the convection section and adding the mixed C4 olefins to the outlet of the radiant section as part of the feed stock in Example 1, the yield of butadiene is increased by 21.49% over the prior art.

Moreover, the pressure drops from the inlet to the outlet in the final operational stage of the hybrid heating segment in Comparative Example 1 and Example 1 are respectively 122.7 kPa and 123.9 kPa. That is to say, by adding olefins to form the first stream in Example 1, the pressure drop in the final operational stage of the hybrid heating segment is merely increased by 0.98% over Comparative Example 1.

Furthermore, from the data in Tables 3 and 5, it can be seen that although the pressure drop from the inlet to the outlet of the transfer line exchange in the final operational stage is slightly increased over that in Comparative Example 1 (respectively 24.9 kPa/g and 23.8 kPa/g in Example 1 and Comparative Example 1), the temperatures at the outlet of the transfer line exchange are decreased from the initial stage to the final stage in view of the coil inlet temperatures thereof.

Therefore, according to the process provided by the present disclosure, the introduction of the mixture composed of steam and the monoolefin-containing stream in the convection section 10 and the outlet of the radiant section 9 does not significantly increase the amount of coke generated in the preheating procedure in the convection 10 due to injection of olefins, nor does it block the transfer line exchange due to formation of coke therein. In addition, the heat of the high-temperature flue gas from the radiant section 9 is effectively utilized and the yield of butadiene is even improved.

Example 2

The process of Example 1 (see FIG. 2) is adopted to carry out the steam cracking reaction. But the feeding rate of naphtha is 40,860 kg/h, and in the first stream the injection rate of steam is 22,700 kg/h and the feeding rate of the mixed C4 olefins is 4,540 kg/h. In the second stream, the injection rate of steam is 2,270 kg/h and the feeding rate of the mixed C4 olefins is 1,362 kg/h. The temperatures of the preheated first and second streams are respectively 530° C. and 560° C. The crossover temperature (XOT) is 596° C. and the temperature at the outlet of the cracking furnace (COT) is 830° C. The cracking reaction time in the radiant section 9 is 0.3 s. Other process parameters of the cracking furnace and transfer line exchange 7 are listed in Table 7. The cracked gases are separated and analyzed and the composition thereof is shown as in Table 8.

TABLE 7

| Feed stock Operational stage | Flow (kg/h) Initial stage to final stage | Temperature (° C.) Initial stage | Temperature (° C.) Final stage | Pressure (kPa-g) Initial stage | Pressure (kPa-g) Final stage |
|---|---|---|---|---|---|
| Inlet of the material preheating segment | 40,860 | 60 | 60 | 510.2 | 539.2 |
| Outlet of the material preheating segment | | 184 | 188 | 495.7 | 513.5 |
| Inlet of the hybrid heating segment | 68,100 | 274 | 296 | 495.7 | 513.5 |
| Outlet of the hybrid heating segment | | 590 | 605 | 384.8 | 389.6 |
| Inlet of the transfer line exchange | 71,732 | 820 | 824 | 80.2 | 89.7 |
| Outlet of the transfer line exchange | | 397 | 450 | 64.8 | 64.8 |

TABLE 8

| Composition | Content (wt %) |
|---|---|
| Hydrogen | 0.95 |
| Methane | 11.48 |
| Ethane | 3.01 |
| Ethylene | 26.81 |
| Acetylene | 0.32 |
| Propane | 0.44 |
| Propylene | 16.42 |
| Methyl acetylene | 0.29 |
| Propadiene | 0.21 |
| Iso-butane | 0.04 |
| N-butane | 0.34 |
| Butene-1 | 2.43 |
| Isobutene | 2.76 |
| Trans-butene | 2.25 |
| Cis-butene | 2.42 |
| Butadiene | 6.60 |
| Others | 23.23 |
| Total | 100.00 |

Example 3

The cracking furnace as shown in FIG. 3 is adopted for the cracking reaction. The specific process comprises:

The C4 olefins 16 with the composition as shown in Table 2 are added into the evaporator for vaporization and mixed C4 olefins of 180° C. are obtained. The mixed C4 olefins are then mixed with hydrogen 18 and steam 3 to obtain a first mixture, which is divided into a first stream and a second stream for the cracking reaction of the present disclosure.

Naphtha 1 of 60° C. (see Table 1 for the corresponding parameters) is preheated in the material preheating segment 11, and steam 3 is simultaneously preheated in the diluted steam superheating segment 13. The preheated naphtha and the preheated steam are mixed and the resulting feed stock mixture is preheated to the crossover temperature in the hybrid heating segment 15 before being mixed with the first stream of the first mixture. The mixed resultant is then injected into the radiant section 9 for cracking reaction. The resulting cracking reaction products are then mixed and reacted with the second stream of the first mixture. The resulting cracking reaction products are injected into the transfer line exchange 7 to be cooled and separated to obtain high-pressure steam and cracked gases, which are fed into subsequent separation devices via the cracked gas main pipe 17. The feeding rate of the naphtha 1 is 43,130 kg/h, and the injection rate of steam in the convection section 10 is 22,700 kg/h. In the first stream of the first mixture, the injection rates of the mixed C4 olefins, hydrogen and steam are respectively 2,270 kg/h, 25 kg/h and 2,270 kg/h. In the second stream of the first mixture, the injection rates of the mixed C4 olefins, hydrogen and steam are respectively 1,362 kg/h, 15 kg/h and 2,270 kg/h. The crossover temperature (XOT) is 590° C. and the temperature at the outlet of the radiant section of the cracking furnace (COT) is 830° C. The cracking reaction time in the radiant section 9 is 0.24 s. Other process parameters of the cracking apparatus are listed in Table 9. The cracked gases are separated and analyzed and the composition thereof is shown as in Table 10.

TABLE 9

| Feed stock Operational stage | Flow (kg/h) Initial stage to final stage | Temperature (° C.) Initial stage | Temperature (° C.) Final stage | Pressure (kPa-g) Initial stage | Pressure (kPa-g) Final stage |
|---|---|---|---|---|---|
| Inlet of the material preheating segment | 43,130 | 60 | 60 | 511.6 | 542.3 |
| Outlet of the material preheating segment | | 184 | 188 | 495.7 | 513.5 |
| Inlet of the hybrid heating segment | 65,830 | 274 | 296 | 495.7 | 513.5 |
| Outlet of the hybrid heating segment | | 590 | 605 | 384.8 | 389.6 |
| Inlet of the transfer line exchange | 74,042 | 820 | 824 | 80.2 | 89.7 |
| Outlet of the transfer line exchange | | 397 | 450 | 64.8 | 64.8 |

TABLE 10

| Composition | Content (wt %) |
|---|---|
| Hydrogen | 0.87 |
| Methane | 11.80 |
| Ethane | 3.15 |
| Ethylene | 27.61 |
| Acetylene | 0.33 |
| Propane | 0.46 |
| Propylene | 16.95 |
| Methyl acetylene | 0.32 |
| Propadiene | 0.25 |
| Iso-butane | 0.01 |
| N-butane | 0.35 |
| Butene-1 | 2.11 |
| Isobutene | 2.73 |
| Trans-butene | 1.00 |
| Cis-butene | 1.53 |
| Butadiene | 5.96 |
| Others | 24.57 |
| Total | 100.00 |

The data in Tables 10 and 6 indicate that the yields of butadiene in Example 3 and Comparative Example 1 are respectively 5.96 wt % and 4.84 wt %. That is, by adding olefins into the inlet and outlet of the radiant section 9 as part of the feed stock in Example 3, the yield of butadiene thereof is increased by 23.14% over the prior art.

Moreover, from the data indicated in Tables 9 and 5, it can be derived that the pressure drop from the inlet to the outlet in the final operational stage of the transfer line exchange 7 in Example 3 and that in Comparative Example 1 are merely slightly different.

Therefore, the introduction of olefins to the outlet of the radiant section 9 does not block the convection section 10 or the transfer line exchange 7 due to formation of coke therein. In addition, the heat of the high-temperature flue gas from the radiant section 9 is effectively utilized and the yield of butadiene is improved.

Example 4

The process of Example 3 is adopted to carry out the steam cracking reaction. But the first mixture is not added to the inlet of the radiant section 9. The feeding rate of naphtha is 45,400 kg/h, and in the convection section 10, the injection rate of steam is 22,700 kg/h. In the first mixture added to the inlet of the radiant section 9, the inventories of the mixed C4 olefins, hydrogen and steam are respectively 2,270 kg/h, 25 kg/h and 2,270 kg/h. The crossover temperature (XOT) is 590° C. and the temperature at the outlet of radiant section of the cracking furnace (COT) is 830° C. The cracking reaction time in the radiant section 9 is 0.3 s. Other process parameters of the convection section 10 and the transfer line exchange 7 are listed in Table 11. The cracked gases are separated and analyzed and the composition thereof is shown as in Table 12.

TABLE 11

| Feed stock Operational stage | Flow (kg/h) Initial stage to final stage | Temperature (° C.) initial stage | Temperature (° C.) Final stage | Pressure (kPa-g) Initial stage | Pressure (kPa-g) Final stage |
|---|---|---|---|---|---|
| Inlet of the material preheating segment | 45,400 | 60 | 60 | 511.6 | 542.3 |
| Outlet of the material preheating segment | | 182 | 187 | 496.5 | 512.3 |
| Inlet of the hybrid heating segment | 68,100 | 274 | 296 | 496.5 | 512.3 |
| Outlet of the hybrid heating segment | | 590 | 605 | 384.8 | 389.6 |
| Inlet of the transfer line exchange | 72,665 | 821 | 825 | 79.8 | 89.3 |
| Outlet of the transfer line exchange | | 399 | 452 | 64.8 | 64.8 |

TABLE 12

| Composition | Content (wt %) |
|---|---|
| Hydrogen | 0.83 |
| Methane | 11.71 |
| Ethane | 3.22 |
| Ethylene | 28.67 |
| Acetylene | 0.33 |
| Propane | 0.45 |
| Propylene | 16.91 |
| Methyl acetylene | 0.31 |
| Propadiene | 0.23 |
| Iso-butane | 0.03 |
| N-butane | 0.35 |
| Butene-1 | 2.28 |
| Isobutene | 2.86 |
| Trans-butene | 1.24 |
| Cis-butene | 1.42 |
| Butadiene | 5.35 |
| Others | 23.81 |
| Total | 100.00 |

Example 5

The process of Example 3 is adopted to carry out the steam cracking reaction. But the first mixture is not added to the outlet of the radiant section 9. The feeding rate of naphtha is 43,130 kg/h and the injection rate of steam in the convection section 10 is 2,270 kg/h. In the first mixture added to the inlet of the radiant section 9, the inventories of the mixed C4 olefins, hydrogen and steam are respectively 2,270 kg/h, 25 kg/h and 1,362 kg/h. The crossover temperature (XOT) is 590° C. and the temperature at the outlet of the radiant section of the cracking furnace (COT) is 830° C. The cracking reaction time in the radiant section 9 is 0.25 s. Other process parameters of the convection section 10 and the transfer line exchange 7 are listed in Table 13. The cracked gases are separated and analyzed and the composition thereof is shown as in Table 14.

TABLE 13

| Feed stock<br>Operational stage | Flow (kg/h)<br>Initial stage to final stage | Temperature (° C.) | | Pressure (kPa-g) | |
|---|---|---|---|---|---|
| | | Initial stage | Final stage | Initial stage | Final stage |
| Inlet of the material preheating segment | 43,130 | 60 | 60 | 511.6 | 542.3 |
| Outlet of the material preheating segment | | 184 | 188 | 495.7 | 513.5 |
| Inlet of the hybrid heating segment | 65.830 | 274 | 296 | 495.7 | 513.5 |
| Outlet of the hybrid heating segment | | 590 | 605 | 384.8 | 389.6 |
| Inlet of the transfer line exchange | 69,487 | 825 | 829 | 78.6 | 88.6 |
| Outlet of the transfer line exchange | | 405 | 463 | 64.8 | 64.8 |

TABLE 14

| Composition | Content (wt %) |
|---|---|
| Hydrogen | 0.88 |
| Methane | 11.78 |
| Ethane | 3.16 |
| Ethylene | 27.61 |
| Acetylene | 0.35 |
| Propane | 0.45 |
| Propylene | 16.94 |
| Methyl acetylene | 0.33 |
| Propadiene | 0.26 |
| Iso-butane | 0.01 |
| N-butane | 0.36 |
| Butene-1 | 2.10 |
| Isobutene | 2.73 |
| Trans-butene | 1.00 |
| Cis-butene | 1.53 |
| Butadiene | 5.94 |
| Others | 24.57 |
| Total | 100.00 |

Through comparisons between and among Tables 9, 11 and 13 and Tables 10, 12 and 14, it can be derived that in Examples 3 to 5 of the present disclosure, the introduction of olefins as partial feed stock at the inlet and outlet of the radiant section 9 not only can enable the heat of the high-temperature flue gas from the radiant section 9 to be effectively utilized, but the yield of butadiene can also be improved.

Example 6

Figure 4:
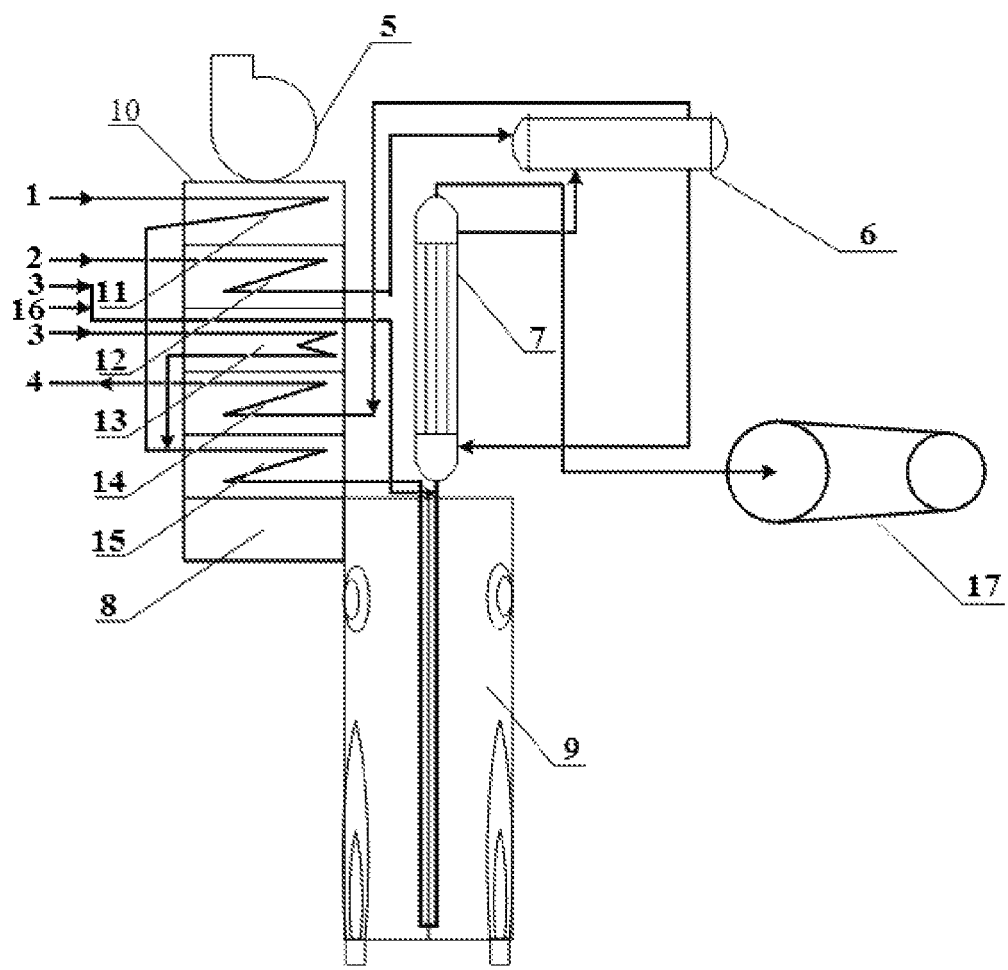
FIG. 4 schematically shows the cracking apparatus and the direction of material flow according to Example 6 of the present disclosure.

The cracking apparatus as shown in FIG. 4 is adopted for the cracking reaction. The specific process comprises:

Naphtha 1 of 60° C. (see Table 1 for the corresponding parameters) is preheated in the material preheating segment 11, and a first stream of steam 3 is simultaneously heated in the diluted steam superheating segment 13. After that, the preheated naphtha and the preheated steam stream are mixed and the resulting feed stock mixture is heated in the hybrid heating segment 15 before entering into the radiant section 9 for cracking reaction. In addition, a second stream of the diluted steam 3 and mixed C4 olefins 16 with the composition as shown in Table 2 are mixed and preheated in the diluted steam superheating segment 13. At the outlet of the radiant section 9, the preheated first mixture is mixed and reacted with the cracking reaction products in the radiant section 9. The resulting final cracking reaction products are injected into the transfer line exchange 7 to be cooled and separated to obtain a high-pressure steam and cracked gases, which are fed into subsequent separation devices via the cracked gas main pipe 17. The feeding rate of the naphtha 1 is 45,400 kg/h, and the injection rate of the first stream of steam is 22,700 kg/h. In the first mixture, the inventories of the mixed C4 olefins and the second stream of steam are respectively 2,270 kg/h and 1,703 kg/h. The temperature of the preheated first stream is 600° C. The crossover temperature (XOT) is 590° C. and the temperature at the outlet of the radiant section of the cracking furnace (COT) is 830° C. The cracking reaction time in the radiant section 9 is 0.24 s. Other process parameters of the cracking furnace and transfer line exchange 7 are listed in Table 15. The cracked gases are separated and analyzed and the composition thereof is shown as in Table 16.

TABLE 15

| | Feed stock | | | | |
|---|---|---|---|---|---|
| Operational stage | Flow (kg/h) | Temperature (° C.) | | Pressure (kPa-g) | |
| | Initial stage to final stage | Initial stage | Final stage | Initial stage | Final stage |
| Inlet of the material preheating segment | 45,400 | 60 | 60 | 511.6 | 542.3 |
| Outlet of the material preheating segment | | 182 | 187 | 496.5 | 512.3 |
| Inlet of the hybrid heating segment | 68,100 | 274 | 296 | 496.5 | 512.3 |
| Outlet of the hybrid heating segment | | 590 | 605 | 384.8 | 389.6 |
| Inlet of the transfer line exchange | 72,073 | 825 | 829 | 79.4 | 88.9 |
| Outlet of the transfer line exchange | | 398 | 452 | 64.8 | 64.8 |

TABLE 16

| Composition | Content (wt %) |
|---|---|
| Hydrogen | 0.86 |
| Methane | 11.56 |
| Ethane | 3.20 |
| Ethylene | 27.99 |
| Acetylene | 0.32 |
| Propane | 0.48 |
| Propylene | 17.23 |
| Methyl acetylene | 0.31 |
| Propadiene | 0.23 |
| Iso-butane | 0.03 |
| N-butane | 0.35 |
| Butene-1 | 2.09 |
| Isobutene | 2.76 |
| Trans-butene | 1.03 |
| Cis-butene | 1.40 |

TABLE 16-continued

| Composition | Content (wt %) |
|---|---|
| Butadiene | 5.56 |
| Others | 24.62 |
| Total | 100.00 |

The data in Tables 16 and 6 indicate that the yields of butadiene in Example 6 and Comparative Example 1 are respectively 5.56 wt % and 4.84 wt %. That is, by adding olefins to the outlet of the radiant section 9 as part of the feed stock in Example 6, the yield of butadiene thereof is increased by 14.88% over the prior art.

Moreover, from the data indicated in Tables 15 and 5, it can be derived that the pressure drop from the inlet to the outlet in the final operational stage of the transfer line exchange 7 in Example 6 and that in Comparative Example 1 are merely slightly different.

Therefore, the introduction of olefins to the outlet of the radiant section 9 as part of the feed stock not only can enable the heat of the high-temperature cracking products to be effectively recycled, but also can avoid the transfer line exchange 7 from being blocked due to formation of coke therein. In addition, the yield of butadiene is significantly improved.

Comparative Example 2

The steam cracking is carried out with the process provided in Example 6 except that the mixed C4 olefins are replaced by naphtha (see Table 2 for the corresponding parameters) of the same weight, wherein other process parameters of the cracking furnace and the transfer line exchange 7 are as indicated in table 17 and the composition of the cracked gases through separation and analysis is shown in Table 18.

TABLE 17

| | Feed stock | | | | |
|---|---|---|---|---|---|
| | Flow (kg/h) | Temperature (° C.) Operational stage | | Pressure (kPa-g) | |
| | Initial stage to final stage | Initial stage | Final stage | Initial stage | Final stage |
| Inlet of the material preheating segment | 45,400 | 60 | 60 | 511.6 | 542.3 |
| Outlet of the material preheating segment | | 182 | 187 | 496.5 | 512.3 |
| Inlet of the hybrid heating segment | 68,100 | 274 | 296 | 496.5 | 512.3 |
| Outlet of the hybrid heating segment | | 590 | 605 | 384.8 | 389.6 |
| Inlet of the transfer line exchange | 72,073 | 825 | 829 | 79.1 | 89.2 |
| Outlet of the transfer line exchange | | 396 | 449 | 64.8 | 64.8 |

TABLE 18

| Composition | Content (wt %) |
|---|---|
| Hydrogen | 0.81 |
| Methane | 11.75 |
| Ethane | 3.41 |
| Ethylene | 29.05 |
| Acetylene | 0.32 |
| Propane | 0.51 |
| Propylene | 16.62 |
| Methyl acetylene | 0.31 |
| Propadiene | 0.25 |
| Iso-butane | 0.03 |
| N-butane | 0.38 |
| Butene-1 | 2.21 |
| Isobutene | 2.95 |
| Trans-butene | 0.01 |
| Cis-butene | 0.53 |
| Butadiene | 4.82 |
| Others | 26.04 |
| Total | 100.00 |

The data in Tables 16 and 18 indicate that the yields of butadiene in Example 6 and Comparative Example 2 are respectively 5.56 wt % and 4.82 wt %. That is, by adding the mixed C4 olefins to the outlet of the radiant section 9 as part of the feed stock in Example 6, the yield of butadiene thereof is increased by 15.35% over the prior art.

Moreover, from the data indicated in Tables 15 and 17, it can be derived that the pressure drops from the inlet to the outlet in the final operational stage of the transfer line exchange in Comparative Example 2 and Example 6 are respectively 24.4 kPa and 24.1 kPa. In addition, the temperature drops from the coil inlet to the outlet of the transfer line exchange in Comparative Example 2 and Example 6 are more or less the same from the initial stage to the in the final stage.

Therefore, it further proves that the introduction of olefins to the outlet of the radiant section 9 as part of feed stock not only enables the heat of the high-temperature cracking products to be effectively recycled, but also avoids the transfer line exchange 7 from being blocked due to formation of coke therein. In addition, the yield of butadiene is significantly improved.

Example 7

The process of Example 6 is adopted to carry out the steam cracking reaction. But the inventories of naphtha and the mixed C4 olefins are respectively 43,130 kg/h and 1,362 kg/h. The injection rates of the first and second streams of steam are respectively 22,700 kg/h and 2,270 kg/h. The temperature of the preheated first mixture is 560° C. The crossover temperature (XOT) is 590° C. and the temperature at the outlet of the radiant section of the cracking furnace (COT) is 830° C. The cracking reaction time in the radiant section 9 is 0.3 s. Other process parameters of the cracking furnace and the transfer line exchange 7 are listed in Table 19. The cracked gases are separated and analyzed and the composition thereof is shown as in Table 20.

TABLE 19

| | Feed stock | | | | |
|---|---|---|---|---|---|
| | Flow (kg/h) | Temperature (° C.) | | Pressure (kPa-g) | |
| | Operational stage | | | | |
| | Initial stage to final stage | Initial stage | Final stage | Initial stage | Final stage |
| Inlet of the material preheating segment | 43,130 | 60 | 60 | 511.6 | 542.3 |
| Outlet of the material preheating segment | | 184 | 188 | 495.7 | 513.5 |
| Inlet of the hybrid heating segment | 65,830 | 274 | 296 | 495.7 | 513.5 |
| Outlet of the hybrid heating segment | | 590 | 605 | 384.8 | 389.6 |
| Inlet of the transfer line exchange | 69,462 | 820 | 824 | 79.6 | 89.1 |
| Outlet of the transfer line exchange | | 397 | 450 | 64.9 | 64.9 |

TABLE 20

| Composition | Content (wt %) |
|---|---|
| Hydrogen | 0.87 |
| Methane | 11.83 |
| Ethane | 3.16 |
| Ethylene | 27.62 |
| Acetylene | 0.32 |
| Propane | 0.47 |
| Propylene | 16.97 |
| Methyl acetylene | 0.33 |
| Propadiene | 0.24 |
| Iso-butane | 0.03 |
| N-butane | 0.34 |
| Butene-1 | 2.10 |
| Isobutene | 2.75 |
| Trans-butene | 1.00 |
| Cis-butene | 1.49 |
| Butadiene | 5.53 |
| Others | 24.95 |
| Total | 100.00 |

Example 8

The process of Example 6 is adopted for the steam cracking except that the first mixture directly added to the outlet of the radiant section 9 is the mixed C4 (see Table 4 for the composition thereof) olefins preheated to 200° C. in the convection section 10. Other parameters of the cracking furnace and the transfer line exchange 7 are indicated in Table 21. The cracked gases are separated and analyzed and the composition thereof is shown in Table 22.

TABLE 21

| | Feed stock | | | | |
|---|---|---|---|---|---|
| | Flow (kg/h) | Temperature (° C.) | | Pressure (kPa-g) | |
| | Operational stage | | | | |
| | Initial stage to final stage | Initial stage | Final stage | Initial stage | Final stage |
| Inlet of the material preheating segment | 45,400 | 60 | 60 | 511.6 | 542.3 |
| Outlet of the material preheating segment | | 182 | 187 | 496.5 | 512.3 |
| Inlet of the hybrid heating segment | 68,100 | 274 | 296 | 496.5 | 512.3 |
| Outlet of the hybrid heating segment | | 590 | 605 | 384.8 | 389.6 |
| Inlet of the transfer line exchange | 70,370 | 825 | 829 | 79.5 | 89.0 |
| Outlet of the transfer line exchange | | 398 | 452 | 64.8 | 64.8 |

TABLE 22

| Composition | Content (wt %) |
|---|---|
| Hydrogen | 0.85 |
| Methane | 11.57 |
| Ethane | 3.21 |
| Ethylene | 28.01 |
| Acetylene | 0.31 |
| Propane | 0.49 |
| Propylene | 17.24 |
| Methyl acetylene | 0.33 |
| Propadiene | 0.25 |
| Iso-butane | 0.02 |
| N-butane | 0.35 |
| Butene-1 | 2.08 |
| Isobutene | 2.77 |
| Trans-butene | 1.05 |
| Cis-butene | 1.42 |
| Butadiene | 5.25 |
| Others | 24.80 |
| Total | 100.00 |

Through comparisons between Examples 6 and 8 and between Tables 16 and 22, it can be derived that compared with merely using the monoolefin-containing stream, when the mixture comprising the monoolefin-containing stream and steam is injected to the outlet of the radiant section 9, better effects, especially higher yield of butadiene can be obtained.

Example 9

The process of Example 1 (see FIG. 2) is adopted to carry out the steam cracking reaction. But the mixed C4 olefins as shown in Table 2 are replaced by the mixed C4 olefins as shown in Table 23, wherein the sum content of propylene and butene is 17.67 wt %. The feeding rate of naphtha 1 is 43,130 kg/h, and in the first stream the injection rate of steam is 22,700 kg/h and the feeding rate of the mixed C4 olefins is 2,270 kg/h. In the second stream, the injection rate of steam is 2,270 kg/h and the feeding rate of the mixed C4 olefins is 1,362 kg/h. The temperatures of the preheated first and second streams are respectively 530° C. and 600° C. The crossover temperature (XOT) is 590° C. and the temperature at the outlet of the radiant section of the cracking furnace (COT) is 830° C. The cracking reaction time in the radiant section 9 is 0.24 s. Other process parameters of the cracking furnace and transfer line exchange 7 are listed in Table 3. The cracked gases are separated and analyzed and the composition thereof is shown as in Table 24.

TABLE 23

| Composition | Content (wt %) | Composition | Content (wt %) |
|---|---|---|---|
| $C_3H_8$ | 0.05 | $i$-$C_4H_8$ | 0.89 |
| $C_3H_6$ | 0.02 | $t$-$C_4H_8$ | 9.66 |
| Propadiene | 0.01 | $c$-$C_4H_8$ | 5.42 |
| $i$-$C_4H_{10}$ | 36.82 | 1,3-$C_4H_6$ | 0.10 |
| $n$-$C_4H_{10}$ | 45.20 | $C_5$++ | 0.13 |
| 1-$C_4H_8$ | 1.68 | $C_6H_6$ | 0.02 |

Total: 100 wt %

TABLE 24

| Composition | Content (wt %) |
|---|---|
| Hydrogen | 0.84 |
| Methane | 12.25 |
| Ethane | 3.25 |
| Ethylene | 28.71 |
| Acetylene | 0.35 |
| Propane | 0.52 |
| Propylene | 17.04 |
| Methyl acetylene | 0.36 |
| Propadiene | 0.27 |
| Iso-butane | 0.01 |
| N-butane | 0.48 |
| Butene-1 | 1.83 |
| Isobutene | 2.38 |
| Trans-butene | 0.87 |
| Cis-butene | 1.32 |
| Butadiene | 5.01 |
| Others | 24.51 |
| Total | 100.00 |

Example 10

The process of Example 1 (see FIG. 2) is adopted to carry out the steam cracking reaction. But the mixed C4 olefins as shown in Table 2 are replaced by the mixed C4 olefins as shown in Table 25, wherein the sum content of propylene and butene is 41.85 wt %. The feeding rate of naphtha 1 is 43,130 kg/h, and in the first stream the injection rate of steam is 22,700 kg/h and the feeding rate of the mixed C4 olefins is 2,270 kg/h. In the second stream, the injection rate of steam is 2,270 kg/h and the feeding rate of the mixed C4 olefins is 1,362 kg/h. The temperatures of the preheated first and second streams are respectively 530° C. and 600° C. The crossover temperature (XOT) is 590° C. and the temperature at the outlet of the radiant section of the cracking furnace (COT) is 830° C. The cracking reaction time in the radiant section 9 is 0.24 s. Other process parameters of the cracking furnace and transfer line exchange 7 are listed in Table 3. The cracked gases are separated and analyzed and the composition thereof is shown as in Table 26.

TABLE 25

| Composition | Content (wt %) | Composition | Content (wt %) |
|---|---|---|---|
| $C_3H_8$ | 0.05 | $i$-$C_4H_8$ | 1.96 |
| $C_3H_6$ | 0.02 | $t$-$C_4H_8$ | 23.40 |
| Propadiene | 0.01 | $c$-$C_4H_8$ | 12.95 |
| $i$-$C_4H_{10}$ | 25.38 | 1,3-$C_4H_6$ | 0.10 |
| $n$-$C_4H_{10}$ | 32.46 | $C_5$++ | 0.13 |
| 1-$C_4H_8$ | 3.52 | $C_6H_6$ | 0.02 |

Total: 100 wt %

TABLE 26

| Composition | Content (wt %) |
|---|---|
| Hydrogen | 0.87 |
| Methane | 12.14 |
| Ethane | 3.24 |
| Ethylene | 28.73 |
| Acetylene | 0.34 |
| Propane | 0.48 |
| Propylene | 16.91 |
| Methyl acetylene | 0.35 |
| Propadiene | 0.26 |
| Iso-butane | 0.03 |
| N-butane | 0.47 |
| Butene-1 | 1.89 |
| Isobutene | 2.45 |
| Trans-butene | 0.89 |
| Cis-butene | 1.36 |
| Butadiene | 5.16 |
| Others | 24.43 |
| Total | 100.00 |

Example 11

The process of Example 1 (see FIG. 2) is adopted to carry out the steam cracking reaction. But the mixed C4 olefins as shown in Table 2 are replaced by the mixed C4 olefins as shown in Table 27, wherein the content of the monoolefin butene is 91.29 wt %. The feeding rate of naphtha 1 is 43,130 kg/h, and in the first stream the injection rate of steam is 22,700 kg/h and the feeding rate of the mixed C4 olefins is 2,270 kg/h. In the second stream, the injection rate of steam is 2,270 kg/h and the feeding rate of the mixed C4 olefins is 1,362 kg/h. The temperatures of the preheated first and second streams are respectively 530° C. and 600° C. The crossover temperature (XOT) is 590° C. and the temperature at the outlet of the radiant section of the cracking furnace (COT) is 830° C. The cracking reaction time in the radiant section 9 is 0.24 s. Other process parameters of the cracking furnace and transfer line exchange 7 are listed in Table 3. The cracked gases are separated and analyzed and the composition thereof is shown as in Table 28.

TABLE 27

| Composition | Content (wt %) | Composition | Content (wt %) |
|---|---|---|---|
| $C_3H_8$ | 0.00 | $i$-$C_4H_8$ | 4.22 |
| $C_3H_6$ | 0.00 | $t$-$C_4H_8$ | 54.39 |
| Propadiene | 0.00 | $c$-$C_4H_8$ | 22.36 |
| $i$-$C_4H_{10}$ | 2.35 | 1,3-$C_4H_6$ | 0.00 |
| $n$-$C_4H_{10}$ | 6.28 | $C_5$++ | 0.1 |
| 1-$C_4H_8$ | 10.30 | $C_6H_6$ | 0.00 |

Total: 100 wt %

TABLE 28

| Composition | Content (wt %) |
| --- | --- |
| Hydrogen | 0.88 |
| Methane | 11.72 |
| Ethane | 3.19 |
| Ethylene | 27.99 |
| Acetylene | 0.33 |
| Propane | 0.47 |
| Propylene | 16.85 |
| Methyl acetylene | 0.31 |
| Propadiene | 0.23 |
| Iso-butane | 0.02 |
| N-butane | 0.35 |
| Butene-1 | 2.05 |
| Isobutene | 2.67 |
| Trans-butene | 0.97 |
| Cis-butene | 1.48 |
| Butadiene | 5.98 |
| Others | 24.51 |
| Total | 100.00 |

LIST OF REFERENCE 1 liquid feed stock;
2 boiler feedwater;
3 steam;
4 high-pressure steam;
5 blower;
6 steam drum;
7 transfer line exchange;
8 flue gas across section;
9 radiant section;
10 convection section;
11 material preheating segment;
12 boiler feedwater preheating segment;
13 diluted steam superheating segment;
14 high pressure steam superheating segment;
15 hybrid heating segment;
16 monoolefin-containing stream;
17 cracked gas main pipe;
18 hydrogen.

What is claimed is:

1. A steam cracking process, comprising
providing a liquid feed stock, a monoolefin-containing stream, and a first mixture, respectively, wherein the monoolefin-containing stream is a hydrocarbon stream comprising at least one selecting from a group consisting of ethylene, propylene, butene, pentene and hexene, the sum content of ethylene, propylene, butene, pentene and hexene accounting for more than 10% by weight of the hydrocarbon stream, and the first mixture is a mixture comprising the monoolefin-containing stream and at least one of steam and hydrogen;
heating the liquid feed stock in a convection section of a cracking furnace and subsequently conveying the heated liquid feed stock to a radiant section of the cracking furnace for cracking reaction therein, wherein the monoolefin-containing stream is conveyed to the cracking furnace for cracking reaction through at least one of the following modes:
Mode B: feeding the monoolefin-containing stream or the first mixture to an inlet of the radiant section thereby mixing the monoolefin-containing stream or the first mixture with an effluent from the convection section; and
Mode C: feeding the monoolefin-containing stream or the first mixture to an outlet of the radiant section thereby mixing the monoolefin-containing stream or the first mixture with products of a first cracking reaction occurring in the radiant section and performing a second cracking reaction at the outlet of the radiant section.

2. The process according to claim 1, wherein the monoolefin-containing stream is a hydrocarbon stream with the sum content of ethylene, propylene, butene, pentene and hexene accounting for more than 30% by weight of the hydrocarbon stream.

3. The process according to claim 1, wherein in Modes B and C, the monoolefin-containing stream, hydrogen, steam and any mixtures thereof are all separately and optionally preheated to a temperature in a range from 120 to 660° C. in the convection section.

4. The process according to claim 1, wherein in Modes B and C, the monoolefin-containing stream is separately used and is preheated to a temperature ranging from 120 to 250° C. before entering into the radiant section.

5. The process according to claim 1, wherein in Modes B and C, the first mixture is the mixture of the monoolefin-containing stream and steam, and the preheated temperature thereof before entering into the radiant section is in a range from 500 to 660° C.

6. The process according to claim 1, wherein in Mode B, the dosage of the monoolefin-containing stream to the liquid feed stock ranges from 0.001:1 to 0.5:1 by mass.

7. The process according to claim 1, wherein in Mode C the dosage ratio of the monoolefin-containing stream to the liquid feed stock ranges from 0.001:1 to 0.2:1 by mass.

8. The process according to claim 1, wherein in Modes B and C, in the first mixture, the mass ratio of the monoolefin-containing stream to hydrogen ranges from 50:1 to 1,000:1, and/or
in the first mixture the mass ratio of the monoolefin-containing stream to steam ranges from 0.1:1 to 10:1.

9. The process according to claim 1, wherein conditions of the first cracking reaction comprise: an initial cracking temperature in a range from 560 to 660° C.; an outlet temperature of the radiant section in a range from 780 to 850° C.; and a reaction time in a range from 0.1 to 0.5 s.

10. The process according to claim 1, wherein the liquid feed stock comprises naphtha and/or hydrogenated cracking residue.

11. The process according to claim 1, wherein the monoolefin-containing stream is a hydrocarbon stream the sum content of butene, pentene and hexane accounting for more than 50% by weight of the hydrocarbon stream.

12. The process according to claim 1, wherein the monoolefin-containing stream is a hydrocarbon stream the sum content of 1-butene and 2-butene accounting for more than 50% by weight of the hydrocarbon stream.

13. The process according to claim 3, wherein in Modes B and C, the monoolefin-containing stream, hydrogen, steam and any mixtures thereof are all separately and optionally preheated to a temperature in a range from 150 to 620° C. in the convection section.

14. The process according to claim 4, wherein in Modes B and C, the monoolefin-containing stream is separately used and is preheated to a temperature ranging from 150 to 200° C. before entering into the radiant section.

15. The process according to claim 5, wherein in Modes B and C, the first mixture is the mixture of the monoolefin-containing stream and steam, and the preheated temperature thereof before entering into the radiant section is in a range from 540 to 620° C.

16. The process according to claim 6, wherein in Mode B, the dosage of the monoolefin-containing stream to the liquid feed stock ranges from 0.01:1 to 0.4:1 by mass.

17. The process according to claim 7, wherein in Mode C the dosage ratio of the monoolefin-containing stream to the liquid feed stock ranges from 0.01:1 to 0.1:1 by mass.

18. The process according to claim 8, wherein in Modes B and C, in the first mixture, the mass ratio of the monoolefin-containing stream to hydrogen ranges from 80:1 to 800:1, and/or in the first mixture the mass ratio of the monoolefin-containing stream to steam ranges from 0.2:1 to 3:1.

19. The process according to claim 9, wherein conditions of the first cracking reaction comprise: an initial cracking temperature in a range from 580 to 640° C.; an outlet temperature of the radiant section in a range from 790 to 840° C.; and a reaction time in a range from 0.2 to 0.3 s.

\* \* \* \* \*